(12) United States Patent
Sato et al.

(10) Patent No.: US 6,568,240 B1
(45) Date of Patent: May 27, 2003

(54) METHOD AND APPARATUS USING A GAS CONCENTRATION SENSOR FOR ACCURATELY CONTROLLING AN AIR FUEL RATIO IN AN INTERNAL COMBUSTION ENGINE

(75) Inventors: Yoshikuni Sato, Aichi (JP); Noboru Ishida, Gifu (JP); Hideki Ishikawa, Aichi (JP); Takafumi Oshima, Aichi (JP); Yasushi Sato, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/480,661

(22) Filed: Jan. 11, 2000

(30) Foreign Application Priority Data

Jan. 11, 1999 (JP) .......................................... 11-004285

(51) Int. Cl.$^7$ .............................................. G01N 27/26

(52) U.S. Cl. ....................................................... 73/1.07

(58) Field of Search ................................ 73/1.02, 1.03, 73/1.06, 1.07, 23.32

(56) References Cited

U.S. PATENT DOCUMENTS

| 4,494,399 A | * | 1/1985 | Youngman ................... 73/1.07 |
| 4,555,930 A | * | 12/1985 | Leach et al. .................. 73/1.07 |
| 4,781,059 A | * | 11/1988 | Suzuki et al. ................. 73/115 |
| 4,924,837 A | | 5/1990 | Chujo et al. |
| 5,823,171 A | | 10/1998 | Farmer et al. |
| 6,202,408 B1 | | 3/2001 | Lepperhoff et al. |

FOREIGN PATENT DOCUMENTS

| DE | 195 19 076 A | 11/1996 |
| DE | 198 10 973 A | 9/1999 |
| EP | 0 089 630 A | 9/1983 |

(List continued on next page.)

OTHER PUBLICATIONS

M. Habaguchi et al, "92 Gasoline Vapor Concentration Sensor—On Board Measurement by Ultrasonic Pulse–", Proceedings for Society of Automotive Engineers of Japan 955 1995–9, pp. 89–92.

M. Sultan et al, "Closed Loop Canister Purge Control System", SAE Paper 980206, Feb. 1998.

European Search Report to EP 00 30 0139 dated Oct. 18, 2002.

Office Action dated Jun. 4, 2002 for Japanese Patent Application No. Hei. 11–4285 and English language translation thereof.

*Primary Examiner*—Robert Raevis
(74) *Attorney, Agent, or Firm*—Sughrue Mion, PLLC

(57) ABSTRACT

The present invention provides a method and apparatus using a gas concentration sensor for accurately controlling an air fuel ratio in an internal combustion engine, featuring in that before the fuel-vaporized gas purged from the canister enters into the intake manifold whereat the sensor detects the gas concentration of the purged gas, the sensor is adjusted so as to adjust a zero point (or zero output level) of the sensor output. In step 100 of FIG. 7, a judgment is made as to whether the flow rate of air reaches a predetermined level. In step 110, processing for zero-point correction of the gas concentration sensor is performed. Specifically, in a state in which the purge valve 17 is closed, concentration of purge gas is measured by use of the gas concentration sensor 4, and a sensor output S1 at that time is obtained. Subsequently, the sensor output S1 is compared with a correct sensor output S0 in order to obtain a difference ΔS therebetween. Accordingly, during subsequent gas concentration measurement, a value S3 obtained through subtraction of the difference ΔS from an obtained sensor output S2 is used as a correct sensor output. In step 120, a supply amount of purge gas, i.e., a concentration of the purge gas to be supplied is obtained. In subsequent step 130, the purge valve 17 is driven in order to supply purge gas to the intake pipe 2 in a required amount (A%).

15 Claims, 8 Drawing Sheets

FOREIGN PATENT DOCUMENTS

| | | |
|---|---|---|
| EP | 0 571 783 A | 12/1993 |
| JP | 1-107142 | 4/1989 |
| JP | 4-204371 | 7/1992 |
| JP | 5-332208 | 12/1993 |
| JP | 7-190980 | 7/1995 |
| JP | 7-260732 | 10/1995 |
| JP | 8-94593 | 4/1996 .......... G01N/29/18 |
| JP | 8-105865 | 4/1996 .......... G01N/29/18 |
| JP | 9-032661 | 2/1997 |

* cited by examiner

METHOD AND APPARATUS USING A GAS CONCENTRATION SENSOR FOR ACCURATELY CONTROLLING AN AIR FUEL RATIO IN AN INTERNAL COMBUSTION ENGINE

BACKGROUND OF THE INVENTION

1. Field of the Invention

The present invention relates to a method and apparatus for controlling an air fuel ratio by using a gas concentration sensor in a fuel supply system for an internal combustion engine, particularly to a method and apparatus for measuring a gas concentration of a combustible gas such as a gasoline vapor gas purged from a canister and mixed with an intake air that is supplied to an intake manifold of an internal combustion engine cylinder by opening a throttle valve, the sensor being placed between the engine cylinder and an inlet for the vapor gas that is purged from the canister and introduced downstream of the throttle valve.

2. Related Art

Conventionally, a fuel supply system for supplying fuel from a fuel tank to the internal combustion engine includes a first supply system which functions in a manner that a fuel liquid such as gasoline is pumped from the fuel tank through a fuel pipe to a fuel injector fixed to an internal combustion engine cylinder by means of a fuel pump.

The fuel supply system further includes a second supply system which functions in a manner that a fuel vapor generated in the fuel tank is temporarily adsorbed or stored by a canister and then the fuel vapor is purged by the canister and sent as a purge gas to the intake manifold so as to be mixed with an intake air entering from the throttle valve.

In other words, in addition to the fuel liquid injected from the injector to the engine cylinder, the fuel vapor vaporized from the fuel tank is purged and mixed with the intake air to form a mixture gas that injects the fuel liquid to be atomized in the engine cylinder. Such fuel vapor vaporized in the fuel tank may be hereinafter referred to as 'purge gas'.

3. Problems to be Solved by the Invention

As a result of supply to the engine of the purge gas in addition to the injected fuel, an air-fuel ratio maintained or determined by a throttle valve, which ratio is controlled based on an injection amount of the fuel is affected or rather deviated from a target value such as a theoretical one, lowering a purification capability of a three-way catalytic exhaust gas purification system for reducing harmful gasses such as CO, HC and NOx.

Further, when the purge gas is used as a main portion of fuel for combustion at the time of starting up the engine and/or when a three-way catalytic converter of the exhaust gas purification system is in an inactive state due to a cold weather, a misfire or incomplete combustion occurs, unless the purge gas concentration is measured with high accuracy and the supply amount of the purge gas is controlled optimally.

Various sensors using surface-characteristics such as an ultrasonic sensor and an oxide semiconductor sensor having electrodes on its surface have been proposed for measuring concentration of such a purge gas contained in the mixture gas before the mixture gas atomizes the liquid fuel by the fuel injector. However, a satisfactory sensor for accurate measurement of the purge gas amount or concentration have not been developed yet, because in addition to variation in output of such a sensor over time, output errors due to adhesion of foreign substances to a surface of the ultrasonic sensor and/or due to moisture and miscellaneous gases contained in the air taken in have always hindered accurate measurement of the purge gas concentration.

Therefore, it has been difficult that a precise or accurate measurement of the purge gas concentration of the gas mixture made of the purge gas and the intake air flowing in the intake manifold or an intake pipe before the liquid fuel is atomized with the gas mixture by fuel injector or before being injected into the engine cylinder.

SUMMARY OF THE INVENTION

The present invention has been accomplished in order to solve the above-described problems.

An object of the present invention is to provide a method and apparatus using a gas concentration sensor for measuring concentration a fuel vapor (or rather purge gas) mixed in an intake air, by which method and apparatus an accurate measurement of concentration of such a fuel-vaporized purge gas entering an intake manifold of an internal combustion engine is attained.

Another object of the present invention is to provide a fuel supply system using a gas concentration sensor for accurately controlling an air fuel ratio for an internal combustion engine, the sensor being disposed in an intake manifold (or an air-intake pipe) which is located between a throttle valve and a fuel injector of the internal combustion engine.

A feature of a method and apparatus using a gas concentration sensor for accurately measuring the vapor gas according to the invention is that before the fuel-vaporized gas purged from the canister enters into the intake manifold whereat the sensor detects the gas concentration of the purged gas, the sensor is adjusted so as to read a zero point (or zero output level) of the sensor output. In other words, when the purge gas stops its flow from the canister, namely when the intake pipe or manifold evacuates the purge gas so that an ambient air enters the intake pipe or manifold, the sensor output is offset reading a zero output of the sensor for measuring the concentration of the specific fuel vaporized gas purged.

Specifically, the present invention provides a method and apparatus using a gas concentration sensor for measuring concentration of a purge gas (i.e. vapor gas vaporized from a liquid fuel) purged and contained in a mixture gas comprised of the purge gas and an ambient air before the mixture gas atomizes the liquid fuel by a fuel injector: wherein the gas concentration sensor is disposed in an intake manifold of an internal combustion engine or a pipe connected to the intake manifold so as to measure concentration of the purge gas; and wherein the concentration of the purge gas is determined by comparing two output values of the gas concentration sensor, the one output value being measured before the purge gas is supplied into the intake manifold or pipe while the other output value being measured after the purge gas is supplied into the intake manifold or pipe. In one aspect of the invention, a degree of degradation or rather deterioration of the gas concentration sensor is pre-checked when the sensor outputs the concentration of the purge gas for computing the concentration. In other words, a zero-point correction of the gas concentration sensor is renewed every time when the purge gas is evacuated from the intake manifold wherein the sensor is placed.

In the present invention, during that the specific purge gas is not supplied from the canister and therefore the concentration of the purge gas to be mixed with the intake air that enters into the fuel injector for atomization of the liquid fuel is supposed to be zero, the output of the gas concentration sensor is preset or offset to be a zero level output(V0) corresponding to a relative gas concentration of 0%.

In actual use, the gas concentration sensor is affected not only by its variation over time but also miscellaneous gases and/or foreign substances including moisture of the air taken in or evaporating from the liquid fuel so that the sensor output often deviates from the preset value (V0) even when the purge gas concentration is 0%. When the sensor output shows a deviation from V0 that corresponds to the specific purge gas concentration of 0%, a certain shift amount (ΔV) namely a subtraction V0 from the sensor output V1 (V1−V0=ΔV) represents either a true value of concentration of the purge gas in the mixture gas or a degraded or deteriorated performance of the sensor due to such variation or influence.

Therefore, the method and apparatus using a gas concentration sensor for measuring the purge gas according to the invention is characterized in that zero-point correction of the sensor output is performed before the sensor output is subjected to computing the purge gas concentration, regardless that the gas concentration sensor has undergone deterioration or deterioration or the like, so as to minimize an offset correction amount.

For example, the sensor output V1 seemingly caused by variation over time or other causes is always subtracted by the shift amount ΔV which is renewed or optimized by the latest offset zero point value V0. (The shift amount ΔV is the latest sensor output V1 subtracted by the V0 measured latest.) Thus, the zero point level V0 of the concentration of the gas sensor to be used for reference is corrected with the newest or latest measured data of V1 that is measured when the purge gas is evacuated from the intake manifold, according to the invention.

In an aspect of the invention, ΔV is taken into consideration in order to eliminate influences of variation over time and the like. V0 (or V1) is an offset output value of the gas concentration sensor when the specific purge gas is absent and the zero-point correction for the sensor is performed on the basis of such V0 and V1.

An alternative way for the zero-point correction may be done by using a mean value that is computed with the at least two offset values V0s (or V1s). An advantage of this alternative way is that when the gas concentration sensor outputs an abruptly varied signal of V0 at one time, an air fuel ratio controller will only use an average value of plural V0 values so as to avoid any risk of such abrupt zero-point reference change.

When the concentration of the specific purge gas is introduced for measurement, the gas concentration is determined by an output value V2(out putted from the sensor) subtracted by the offset value V0 (zero point value) that is corrected by the latest measured offset value (V1).

A second alternative way may be that only when the previously determined offset value (V0) of the gas concentration sensor corresponding to the gas concentration of zero is lower than a certain offset output value (V1)(i.e. when V1>V0) and when the sensor output (V2) corresponding to the specific purge gas concentration becomes higher by ΔV (=V1−V0), the difference (V2−ΔV) is used as a value corresponding to the actual purge gas concentration. The thus determined gas concentration by referring to the output value (V2−ΔV) of the sensor may be advantageously assisted by use of a memory media recording a map wherein the sensor output is illustrated as a function of the actual purge gas concentration of the mixture gas.

The output of the deteriorated gas concentration sensor may be corrected by a plurality of the maps or selectively corrected in accordance with the correction amount.

Once the concentration of the specific purge gas is stably obtained through the zero-point correction, supply of the specific purge gas can be measured precisely for control of the air fuel ratio and/or post-combustion air-fuel ratio control.

Further, a control of the supply of the specific purge gas can be much easily done, according to a method and apparatus of the present invention, if an additional step in which the opening of the purge valve is controlled on the basis of the sensor output so as to regulate the supply (or flow rate) of the purge gas.

Types of the specific purge gases may include a combustible gas such as fuel vapor supplied from a canister into the intake air and unburned gas from an EGR system.

In an aspect of the invention, the method and apparatus using a gas concentration sensor for accurately measuring the purge gas concentration may be characterized in that the offset output of gas concentration sensor output is detected and adjusted during cranking immediately after an ignition key is turned and before the liquid fuel is atomized and injected into the engine cylinder.

An important feature is a timing at which the output of the gas concentration sensor is detected for zero point offset of the sensor. The best timing is during when the intake air serving as a base gas for the air fuel ratio is mixed with no specific purge gas. Such timing is during a cranking period for an engine or during the start-up period in which the activity of the catalytic converter is low. The zero-point correction in which the shift amount of the sensor output is taken into consideration is preferably performed immediately after detection of any degradation of the sensor. It is preferable that the zero-point correction is performed at any time upon measurement of actual gas concentration before the vapor gas is purged from a canister. It may be best to adjust the offset zero point level during a purging operation just after the ignition key is turned.

When the purging operation is first performed after the ignition key is turned, influence of fuel adhering to a purge gas supply passage on the downstream side with respect to the purge valve can be eliminated so as to determine the degree of the deterioration of the gas concentration sensor more accurately, and to perform the zero-point correction more accurately.

The invention also teaches a timing at which the deterioration or degradation of the gas concentration sensor is detected. Such a timing is during a fuel-cut operation in which purging is not performed and only the base gas of the air is taken in.

The detection of the degree of the deterioration of the gas concentration sensor may be performed while a signal from an ECU or one of signals from various sensors mounted on the vehicle is used as a trigger signal.

An ultrasonic sensor using ultrasonic waves such that their speed changes in accordance with the concentration of the specific purge gas in the intake air may be preferably utilized as the gas concentration sensor used in the method and apparatus of the invention. In such a ultrasonic sensor, the ultrasonic waves are transmitted against the intake air and a propagation speed (i.e. propagation time) of the ultrasonic waves is detected in order to determine the concentration of the specific purge gas.

Another type of the gas concentration sensor usable in the method and apparatus of the invention comprises an element formed of oxide semiconductor such as tin oxide and utilizes a phenomenon that the amount of absorbed oxygen on the element surface changes due to oxidation of the specific purge gas on the element surface. A surface electrical resistance of the element changes due to variation in the number of free electrons. The concentration of the specific purge gas is determined through detection of variation in the electrical resistance by electrodes formed on the element surface.

Another sensor for this use may include an element formed of solid electrolyte, in which the concentration of the specific purge gas is determined through detection of a mixed electrode potential relative to a reference electrode, through reaction between the specific purge gas and catalyst coated on the element surface, or through a potential difference which varies according to the Nernst equation.

Other gas concentration sensor possibly utilized for the present invention may be a heater type using e.g. a platinum wire, wherein the amount of heat generated due to oxidation of the specific purge gas on the surface of the platinum wire is detected on the basis of variation in the electrical resistance of the platinum wire so that the concentration of the specific purge gas is determined. Other type of the sensor suitable for the present invention may utilize an electrostatic capacity measured between paired electrodes disposed in a measurement chamber into which the specific purge gas is introduced. The concentration of the specific purge gas is determined through detection of the electrostatic capacity between the paired electrodes at the time when the specific purge gas is introduced.

The present invention provides a controller for an air fuel ratio of an internal combustion engine using the gas concentration sensor, comprising: memory means for storing, as a reference output, an output of the gas concentration sensor when the concentration of the specific purge gas is 0%; actual output detection means for detecting an actual output of the gas concentration sensor on the basis of an output of the gas concentration sensor before the specific purge gas is supplied; and zero-point correction means for comparing the reference output and the actual output in order to correct the zero point of the gas concentration sensor. In this controller according to the invention, the memory means stores therein a reference output-which is an output of the gas concentration sensor when the concentration of the specific purge gas is 0%. The actual output detection means detects an actual output of the gas concentration sensor corresponding to the 0% concentration, on the basis of an output of the gas concentration sensor before the specific purge gas is supplied. Subsequently, the zero-point correction means compares the reference output and the actual output in order to determine the difference therebetween, on the basis of which the zero point of the gas concentration sensor is corrected.

The controller may further comprise a measurement means for determining the concentration of the specific purge gas, on the basis of the output of the gas concentration sensor subjected to the zero-point correction. The concentration of the specific purge gas is determined on the basis of the output of the gas concentration sensor after being subjected to the zero-point correction. Therefore, the concentration of the specific purge gas can be determined accurately, while influences of variation over time and the like are eliminated.

The controller may further comprise an adjustment means (e.g. a purge valve) for adjusting supply of the specific purge gas on the basis of the output of the gas concentration sensor subjected to the zero-point correction. The gas concentration can be measured precisely on the basis of the output of the gas concentration sensor after being subjected to the zero-point correction. Therefore, a required amount of the specific purge gas can be supplied accurately through control of adjustment means performed on the based of the precise gas concentration.

DESCRIPTION OF SYMBOLS

Figure 1:
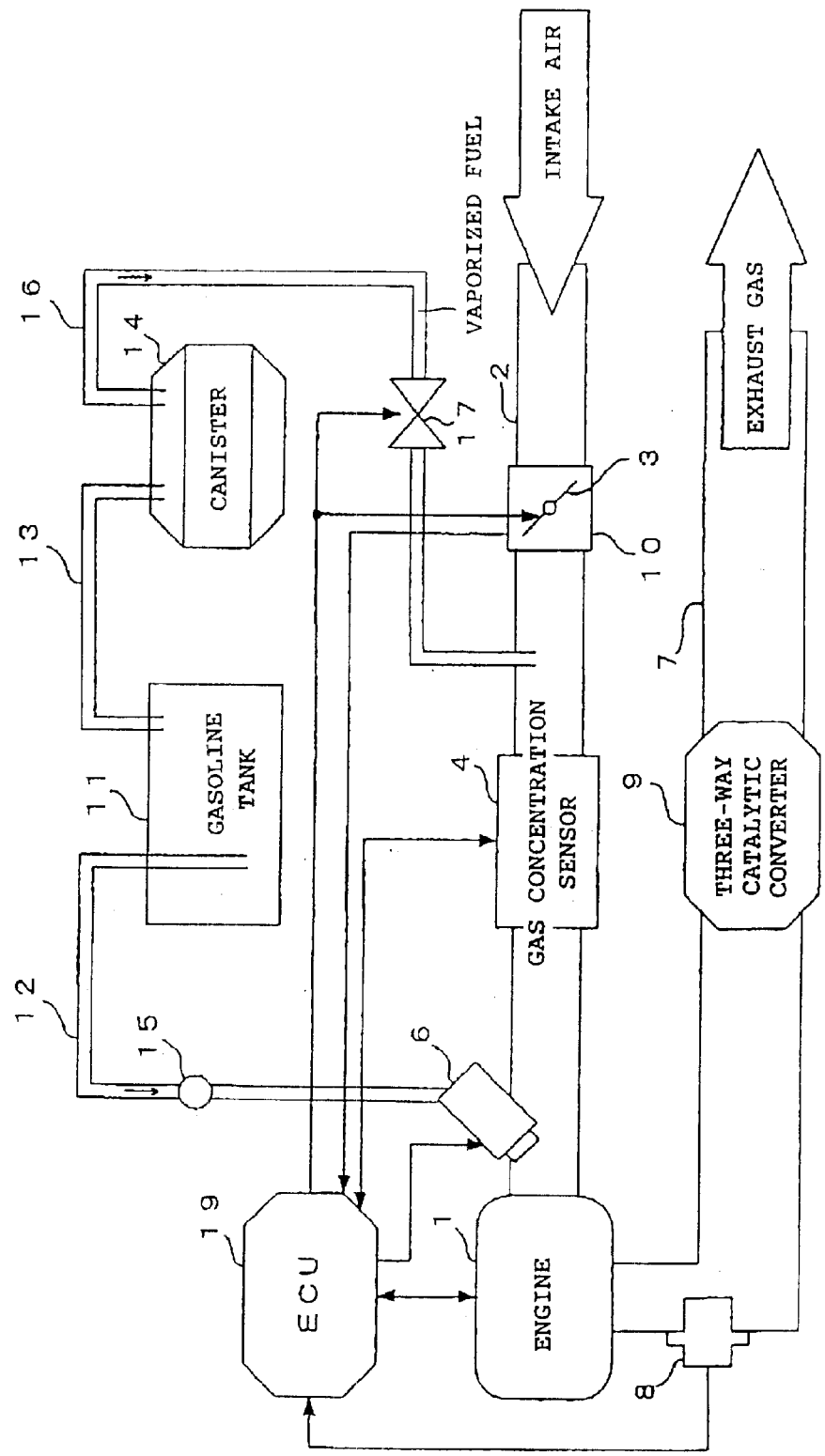
FIG. 1 is a system diagram showing an entire system comprising a controller for a gas concentration sensor provided in an intake pipe of an internal combustion engine, wherein an output of the gas concentration sensor is corrected according to the invention.

1: engine
2: intake pipe
3: throttle valve
4: gas concentration sensor
6: injector
7: exhaust pipe
8: oxygen sensor
9: three way catalytic converter
10: air flow meter
11: gasoline tank
12: first supply path
13: second supply path
14: canister
16: third supply path
17: purge valve
19: electronic control unit (ECU)

DETAILED DESCRIPTION OF THE INVENTION

Embodiments of a method and apparatus using a gas concentration sensor and a controller according to the present invention will now be described with reference to the drawings.

1. First Embodiment:

An embodiment according to the present invention is directed to a technique for measuring concentration of vaporized fuel by use of a gas concentration sensor utilizing ultrasonic waves.

a) First, the configuration of a system according to the present embodiment will be described.

FIG. 1 is a diagram showing a system configuration including a gas concentration sensor and a controller therefor.

As shown in FIG. 1, in the present embodiment, a throttle valve 3, a gas concentration sensor 4, and an injector 6, from upstream side to downstream side, are disposed on an intake pipe 2 of an engine 1. Meanwhile, an oxygen sensor (full-range-type air-fuel ratio sensor) 8 and a three-way catalytic converter 9, from upstream side to downstream side, are disposed on an exhaust pipe 7 of the engine 1.

Further, a path for supplying fuel to the engine 1 includes a first supply system for supplying liquid fuel and a second supply system for supplying gas fuel.

In the first supply system, a gasoline tank 11 is connected to the injector 6 via a first supply path 12 and a fuel pump 15. Fuel is supplied, through the first supply path 12, from the gasoline tank 11 to the injector 6 by means of the fuel pump 15. Then, fuel is injected into the intake pipe 2 from the injector 6.

In the second supply system, the gasoline tank 11 is connected to a canister 14 via a second supply path 13. The canister 14 is connected, via a third supply path 16 and a purge valve 17, to a portion of the intake pipe 2 extending between the throttle valve 3 and the gas concentration sensor 4. Accordingly, fuel which has evaporated from the gasoline tank 11 is once adsorbed by the canister 14. Outside air is introduced as appropriate into the canister 14 to thereby purge fuel (vaporize fuel from the canister 14). The thus-purged vaporized fuel (purge gas) undergoes flow regulation in the purge valve 17 and is then supplied into a portion of the intake manifold or pipe 2 extending between the throttle valve 3 and the gas concentration sensor 4.

This system employs an electronic control unit (ECU) 19 in order to control purge gas supply and air-fuel ratio. The ECU 19 receives signals from various sensors, such as the gas concentration sensor 4, the oxygen sensor 8, and an air flow meter 10. The ECU 19 outputs control signals to various actuators, such as the purge valve 17, the throttle valve 3, and the injector 6. The ECU 19 also outputs a control signal, such as an on-off signal, to the gas concentration sensor 4.

b) Next, the structure and principle of the gas concentration sensor 4 will be described.

Figure 2:
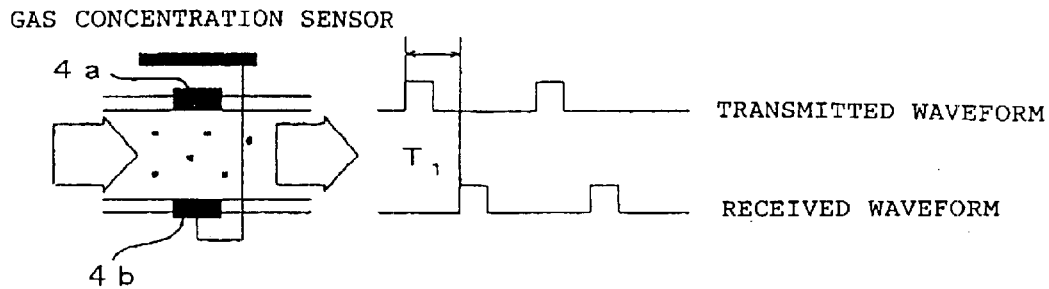
FIG. 2(a) is an explanatory view showing a principle of measurement of the gas concentration sensor used in the system as shown in FIG. 1, wherein a purge gas is not fed into the intake pipe through a tubular pipe of the gas concentration sensor having an ultrasonic sensor on the tubular pipe according to a first embodiment of the invention.
FIG. 2(b) is an explanatory view showing a principle of measurement of the gas concentration sensor used in the system as shown in FIG. 1, wherein a purge gas is fed into the intake pipe through a tubular pipe of the gas concentration sensor having an ultrasonic sensor on the tubular pipe according to a first embodiment of the invention.
Figure 2:
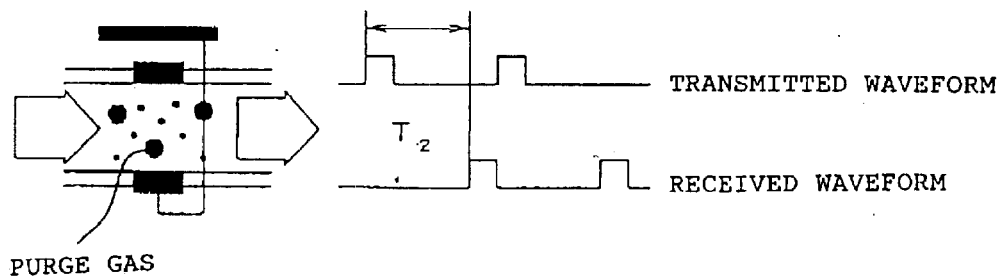

The gas concentration sensor 4 used in the present embodiment is an ultrasonic-type gas concentration sensor utilizing an ultrasonic element which generates ultrasonic waves by use of a piezoelectric element. As shown in FIG. 2, the gas concentration sensor 4 comprises an ultrasonic transmitter element 4b and an ultrasonic receiver element 4a disposed perpendicular to the passage of intake air. Any element capable of transmitting and receiving ultrasonic waves may be used as the gas concentration sensor 4.

When concentration measurement is performed by use of the gas concentration sensor 4, the transmitter element 4b is operated to transmit an ultrasonic wave, and the receiver element 4a is operated to receive the ultrasonic wave. At this time, the waveform of the received ultrasonic wave shifts relative to the waveform of the transmitted ultrasonic wave, by a propagation time corresponding to the concentration of purge gas contained in intake air. For example, as shown in FIG. 2(a), when the concentration of the purge gas is low, the propagation time—which is the lag by which the waveform of the received ultrasonic wave shifts relative to the waveform of the transmitted ultrasonic wave—becomes small (T1). Meanwhile, as shown in FIG. 2(b), when the concentration of the purge gas is high, the propagation time becomes large (T2). Therefore, the gas concentration can be detected on the basis of a sensor output which reflects the propagation time.

Figure 3:
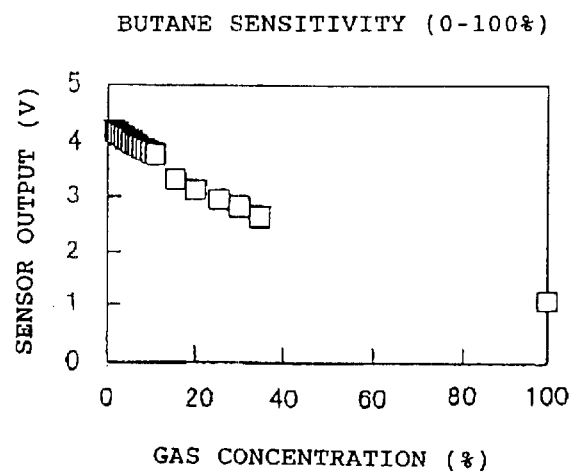
FIG. 3 is a graph showing a sensitivity characteristic of a gas concentration sensor having an ultrasonic element, when a butane gas is fed into the intake pipe.

In an exemplary case in which vaporized fuel is butane, as shown in FIG. 3, there exists a linear relationship between sensor output and gas concentration. Accordingly, the gas concentration of the vaporized fuel can be measured on the basis of the sensor output. It is to be noted that FIG. 3 shows the case where intake air is in a dry state (absolute humidity: 0%).

c) Next, the principle of zero-point correction (offset adjustment) of the gas concentration sensor 4 will be described.

In the case of the gas concentration sensor 4 of the above-described ultrasonic type, the sensor accuracy deteriorates due to the following factors; i.e., (1) $H_2O$ (moisture) content and (2) deposits on the sensor:

(1) When content of $H_2O$ (moisture), having a smaller molecular weight than does air, increases, propagation speed increases (propagation time decreases), with the result that the sensor output increases and the apparent butane concentration decreases.

Figure 4:
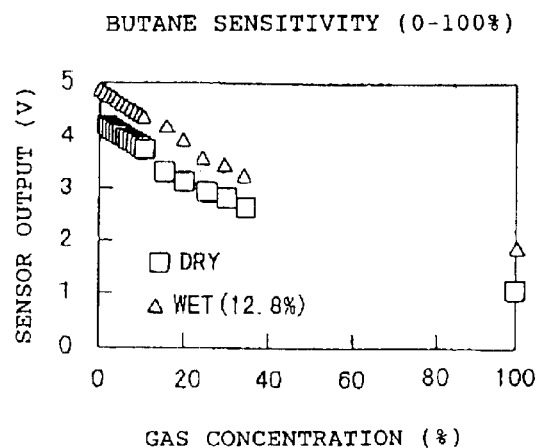
FIG. 4 is a graph showing a difference of the sensitivity characteristics of the gas concentration sensor having an ultrasonic element, wherein one sensitivity characteristic shows when a dry gas is fed into the intake pipe and the other sensitivity characteristic shows when a wet or humid gas is fed into the intake pipe indicating a necessity of zero-point correction according to the invention.

In FIG. 4 showing a butane-sensitivity characteristic, the characteristic for the case where intake air is dry (DRY; absolute humidity: 0%) is represented by use of white square blocks, and the characteristic for the case where intake air has a high level of humidity (WET; absolute humidity: 12.5%, relative humidity at 50° C.: about 99 RH%) is represented by use of white triangular blocks. As is apparent from FIG. 4, when the humidity increases, the sensor output increases, with a resultant decrease in apparent butane concentration.

Figure 5:
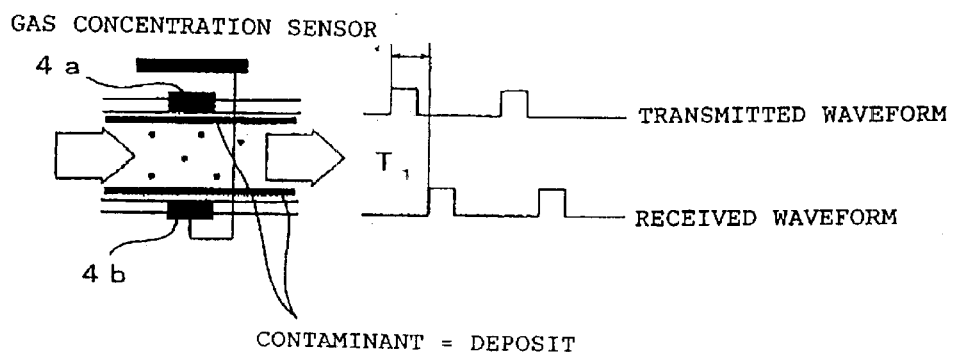
FIG. 5(a) is an explanatory view showing a gas concentration sensor having ultrasonic elements, wherein an inner wall of the gas concentration sensor is deposited with a foreign material product thereby causing acoustic acceleration between the ultrasonic elements and an inaccurate measurement of the gas flowing inside the inner wall.
FIG. 5(b) is an explanatory view showing a gas concentration sensor having ultrasonic elements, wherein an inner wall of the gas concentration sensor is not deposited with a foreign material product.
Figure 5:
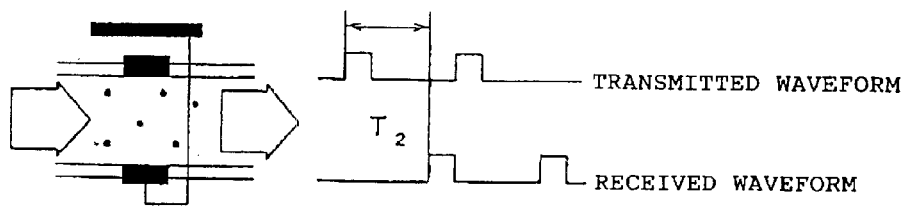

(2) As shown in FIG. 5(a), when a solid substance (deposit) is present on the surface or the like of the transmitter element 4b and the receiver element 4a of the gas concentration sensor 4, ultrasonic waves propagate through the deposit at a higher propagation speed, so that the propagation time becomes shorter. As a result, the propagation time T1 in this case becomes shorter than the propagation time T2 in the case shown in FIG. 5(b) in which no deposit is present. Therefore, as in the above-described case (1), the sensor output increases, with a resultant decrease in apparent butane concentration.

Accordingly, in the present embodiment, zero-point correction (offset adjustment) of the gas concentration sensor 4 is performed in consideration of the above-described characteristics.

Specifically, when an ignition key is turned and thus intake air is introduced into the engine 1, purge-gas concentration measurement is performed in a state in which purge gas is not introduced into the intake pipe.

In this state, since no purge gas is present within the intake air, the output of the gas concentration sensor 4 must become about 4.2 V, which indicates that the concentration of purge gas is 0%. However, when the above-described moisture or deposit affects the sensor, the sensor output changes as shown in FIG. 4.

Accordingly, when the concentration of purge gas is measured in a state in which purge gas is actually supplied, errors of the sensor output are corrected (zero-point correction) in order to accurately measure gas concentration.

Figure 6:
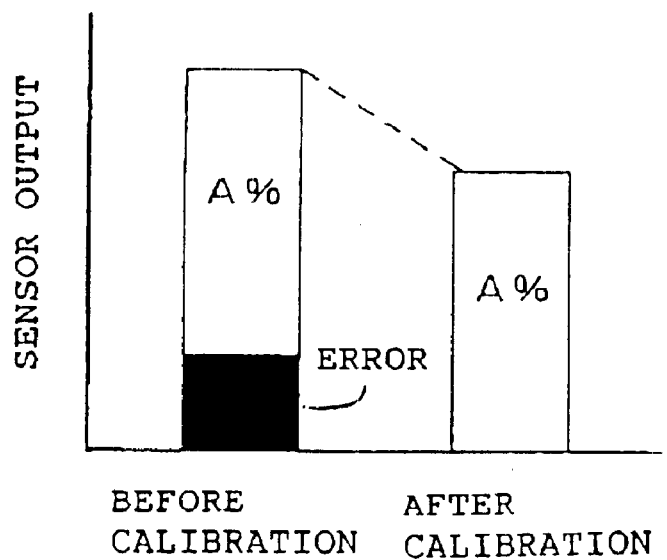
FIG. 6 is an explanatory illustration showing a variation in a sensor output due to zero-point correction, according to the invention.
Figure 7:
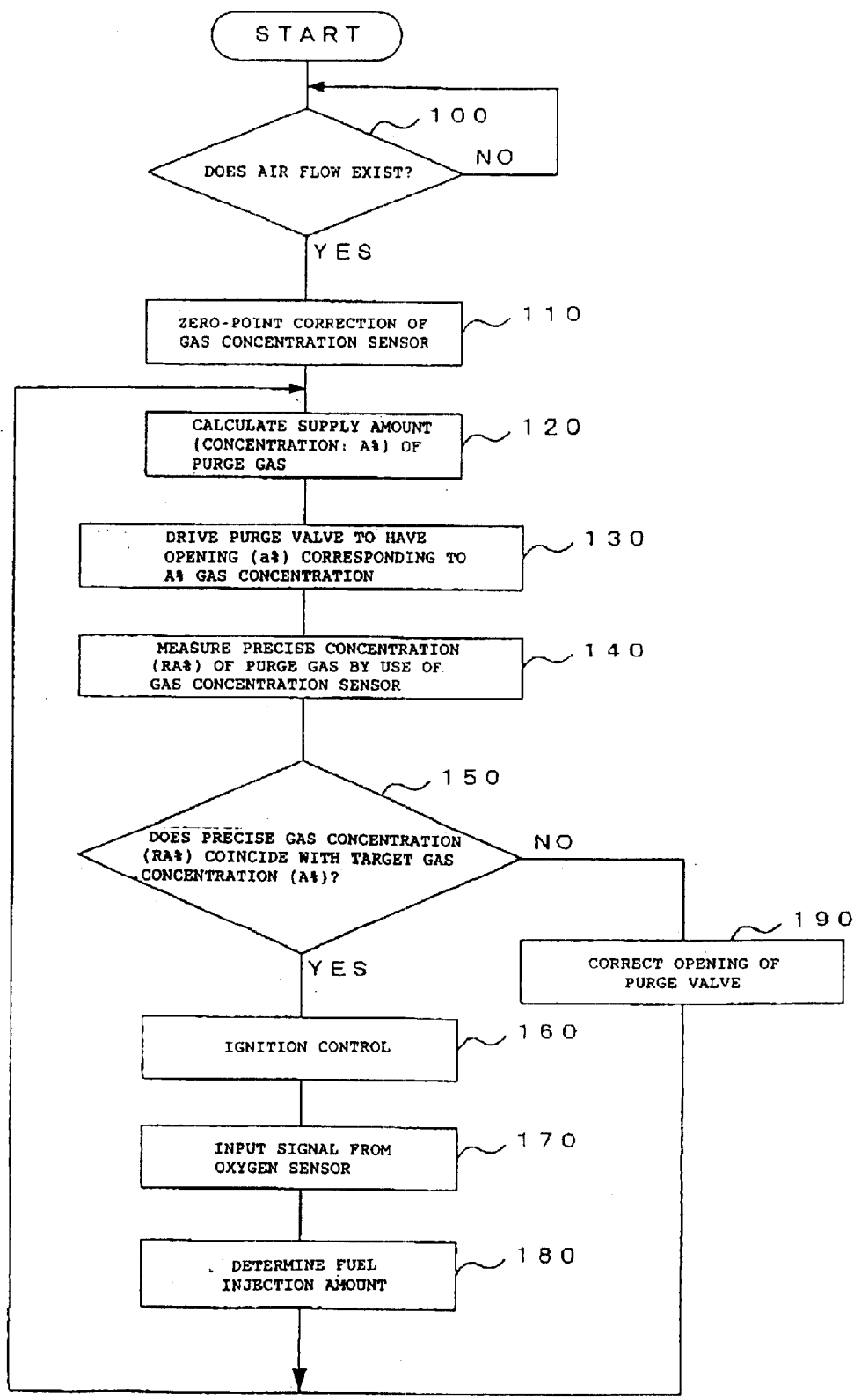
FIG. 7 is a flowchart showing a control process for controlling a fuel injection amount, wherein an output of a gas concentration sensor provided in an intake pipe is corrected based on a zero point correction before a purge gas is supplied into the intake pipe according to the invention.

In an exemplary case shown in FIG. 6 in which the sensor outputs 4.8 V when no purge gas is present (before calibration), a difference (0.6 V) between the output and a correct output (4.2 V) is first obtained as an error. When purge gas is supplied to the intake pipe and the concentration of the purge gas is measured, the output of the sensor is corrected in consideration of the error (in this case, 0.6 V is subtracted from the output). A gas concentration (A%) is obtained on the basis of the thus-corrected sensor output (after calibration).

d) Next, among processing performed in the ECU 19, processing in relation to the gas concentration sensor 4 will be described with reference to the flowchart shown in FIG. 7.

When the ignition key is turned (key-on) in order to start the engine 1, or during cranking, in step 100, a judgment is made, on the basis of a signal from the air flow meter 10, as to whether the flow rate of air reaches a predetermined level. When the result of the judgment is Yes, the processing proceeds to step S110.

In step 110, processing for zero-point correction of the gas concentration sensor 4 is performed.

Specifically, in a state in which the purge valve 17 is closed, intake gas containing no purge gas is subjected to measurement by use of the gas concentration sensor 4, and a sensor output S1 at that time is obtained. The sensor output S1 involves errors stemming from moisture and variation over time and the like. Subsequently, the sensor output S1 is compared with a correct sensor output S0 in order to obtain a difference ΔS therebetween. The sensor output difference ΔS is stored as correction data for zero-point correction.

Accordingly, during subsequent gas concentration measurement, a value S3 obtained through subtraction of the difference ΔS from an obtained sensor output S2 is used as a correct sensor output.

In subsequent step 120, the supply amount of purge gas; i.e., the concentration (e.g., butane concentration of A%) of purge gas to be supplied is obtained. At the time of start-up, the amount of purge gas to be supplied is determined properly according to the type of the engine, cooling water temperature, etc., and after the start-up, the amount of purge gas to be supplied is determined properly according to the engine speed, etc.

In subsequent step 130, the purge valve 17 is driven in order to supply purge gas to the intake pipe 2 in the above-described required amount (A%).

That is, the ECU 19 stores therein a map which shows the relationship between the opening of the purge valve 17 and the supply amount (e.g., concentration) of purge gas. Therefore, when purge gas must be supplied in an amount of A%, the opening of the purge valve 17 is set to, for example, a% by use of a theoretical (ideal) relationship indicated by line 1 in FIG. 8. Subsequently, the purge valve 17 is driven such that the valve opening becomes a%. The opening of the purge valve 17 is adjusted through control of the duty ratio (D/T) of current for driving the purge valve 17.

In subsequent step 140, in the state in which purge gas has been supplied to the intake pipe, the gas concentration sensor 4 is driven in order to measure the concentration of the purge gas contained in intake air before the purge gas is burned.

In this measurement step, as described above, the difference ΔS for zero-point correction is subtracted from the actual sensor output S2 in order to obtain a correct (precise) sensor output S3. On the basis of the sensor output S3, a precise gas concentration (e.g., RA%) containing no errors is obtained by use of the map representing the relationship of FIG. 3.

In subsequent step S150, a judgment is made as to whether the precise gas concentration (RA%) of purge gas obtained through zero-point correction coincides with a target gas concentration (A%) calculated in step 120. When the result of the judgment is Yes, the processing proceeds to step 160, and when the result of the judgment is No, the processing proceeds to step 190.

In step 160, ignition control is performed in order to burn fuel within a cylinder of the engine 1.

In subsequent step 170, the concentration of oxygen in exhaust gas is measured on the basis of a signal from the oxygen sensor 8, and the air-fuel ratio of the fuel mixture is determined.

In subsequent step 180, the amount of fuel injected from the injector 6 is determined on the basis of the air-fuel ratio, throttle opening, and engine speed. Subsequently, the processing returns to step 120. The injection amount of fuel is obtained through subtraction of the supply amount of purge gas from a required fuel supply amount.

Meanwhile, when the result of the judgment in step 150 is No; i.e., when the precise gas concentration (RA%) of purge gas does not coincide with the target gas concentration (A%), as described above, the processing proceeds to step 190 in order to correct the opening of the purge valve 17 in order to obtain the target gas concentration (A%).

Figure 8:
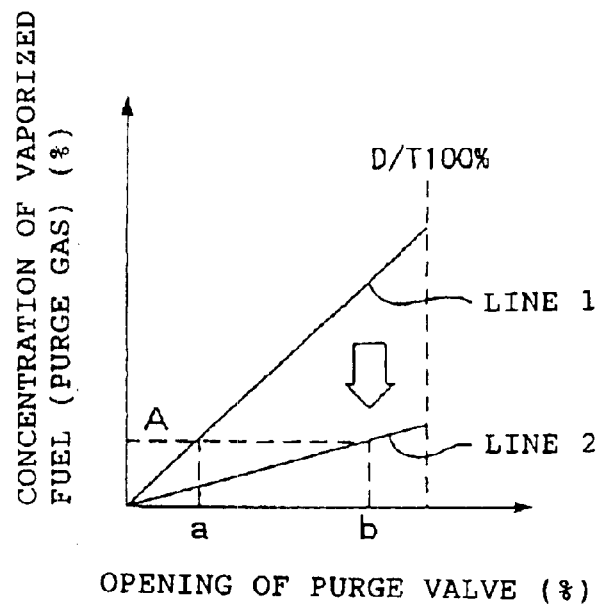
FIG. 8 is a graph showing a relation between a concentration of vaporized fuel and an opening percent of a purge gas valve.

That is, if the relationship between gas concentration and valve opening is a theoretical one as indicated by line 1 in FIG. 8, the target gas concentration (A%) is obtained when the valve opening is controlled to a%. However, in actuality, target gas concentration (A%) cannot be obtained, because the gas concentration on the supply side (e.g., the canister side) is unknown and finite. Therefore, the valve opening is corrected in order to obtain the target gas concentration before combustion.

Specifically, when the actual gas concentration (RA%) is lower than the target gas concentration (A%), the relationship between the gas concentration and the valve opening is changed as indicated by line 2 in FIG. 8, and the purge valve 17 is controlled.in accordance with the thus-changed map. Therefore, in this case, the purge valve 17 is controlled such that the valve opening becomes b%. With this control, a required amount of purge gas is supplied to the intake pipe 2 so as to realize the target gas concentration (A%).

e) Next, a test performed for confirming the effect of the present embodiment will be described.

A car having a straight 6-cylinder, 2.0-liter engine was used as a test vehicle, and the mode was controlled at a frequency of 3 Hz such that the air-fuel ratio $\lambda$ became $1\pm0.03$.

Figure 9:
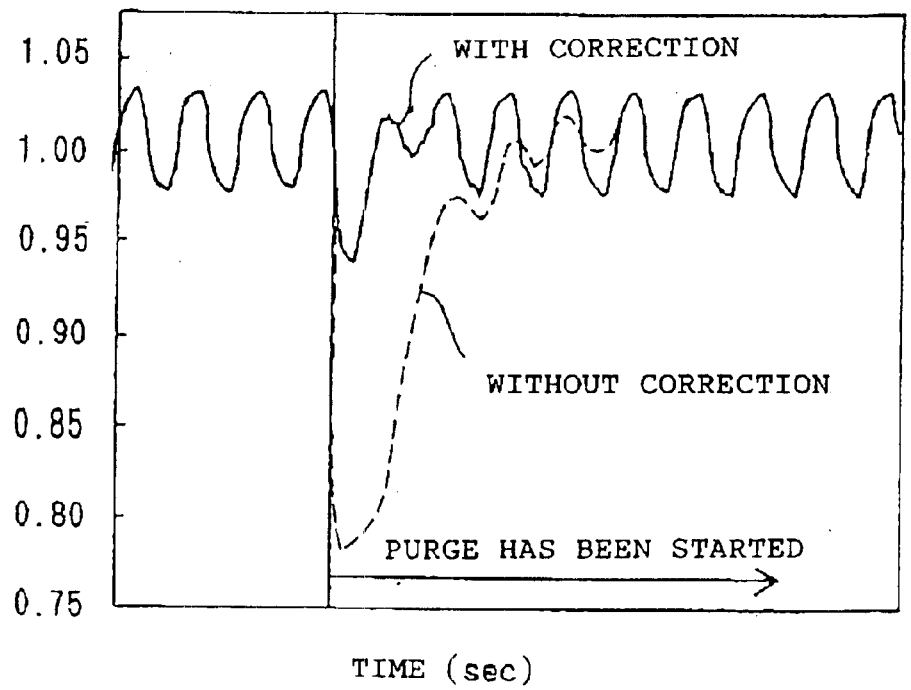
FIG. 9 is a graph showing a test result, wherein an air fuel ratio λ does not critically vary when the present method of using a gas concentration sensor based on a zero-point correction is applied.

The solid line in FIG. 9 shows the test result for the case where zero-point correction was performed, and the broken line in FIG. 9 shows the test result for the case where zero-point correction was not performed.

Vaporized fuel is supplied when the purge valve is opened. At this time, as is apparent from FIG. 9, in the case where zero-point correction is not performed, the sensor output overshoots too much toward the rich side ($\lambda<1$), and the convergence time namely the time required for reaching the target point ($\lambda=1$) increases, which is not preferable.

By contrast, in the case where zero-point correction is performed as in the present embodiment, the degree of overshoot is small and less than 10%, and the convergence time namely the time required for reaching the target point becomes short, which is preferred.

As described above, in the present embodiment, during cranking at the time of key-on, the purge gas concentration measurement is performed before purge gas is supplied, and the zero point of the gas concentration sensor is corrected on the basis of data obtained through the measurement. Therefore, when actual purge gas is supplied, and its gas concentration is measured, the concentration of the purge gas can be measured precisely, while the influence of moisture and deposit is eliminated.

Therefore, when the purge valve 17 is controlled on the basis of the precise gas concentration, a required amount of purge gas can be supplied accurately, so that air-fuel ratio control and other controls can be performed accurately.

2. Second Embodiment:

Next, a second embodiment of the present invention will be described.

The present embodiment differs from the first embodiment in that a different type of a gas concentration sensor is used. Descriptions for the same portions as those of the first embodiment are omitted or simplified.

Figure 10:
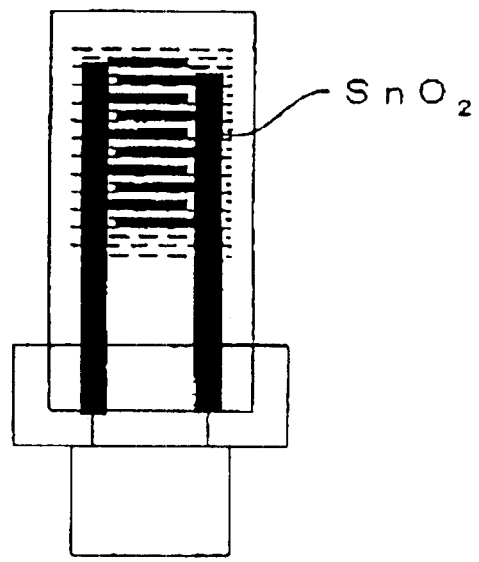
FIG. 10 is an explanatory view showing a gas concentration sensor using a surface resistor between surface electrodes formed on a semiconductor substrate.

The present embodiment employs an oxide semiconductor sensor (specifically, a sensor whose sensitive portion contains tin oxide as a main component) as shown in FIG. 10.

Figure 11:
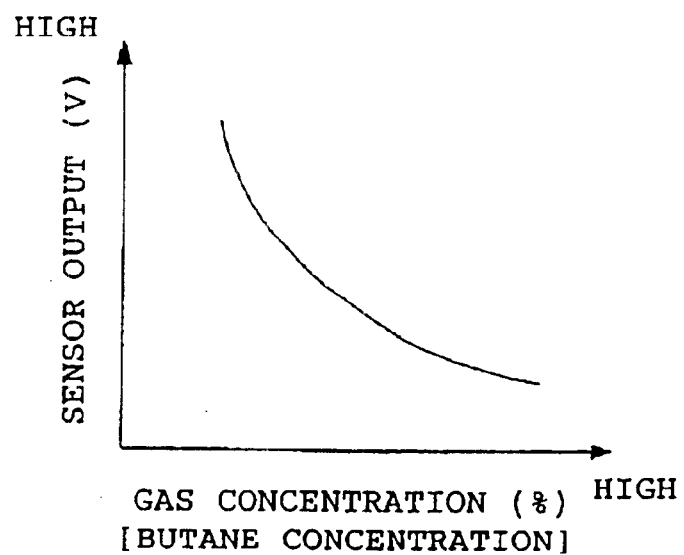
FIG. 11 is a graph showing a relationship between gas concentration and output of such a gas concentration sensor as shown in FIG. 10.

In the oxide semiconductor sensor of the above-described type, as shown in FIG. 11, vaporized fuel (e.g., purge gas) causes oxidation reaction on the surface of the sensor, so that the amount of absorbed oxygen changes, and the electrical resistance of the element changes. As a result, the sensor output changes. The gas concentration (e.g., butane concentration) is measured on the basis of the change in the sensor output.

Figure 12:
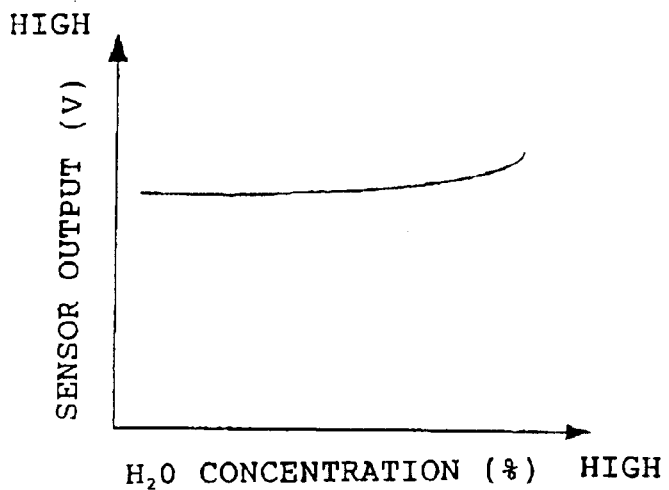
FIG. 12(a) is a graph showing examples of degradation or deterioration in accuracy of the gas concentration sensor as shown in FIG. 10, showing influence of moisture.
FIG. 12(b) is a graph showing degradation or deterioration in accuracy of the gas concentration sensor as shown in FIG. 10, showing influence of variation over time.
Figure 12:
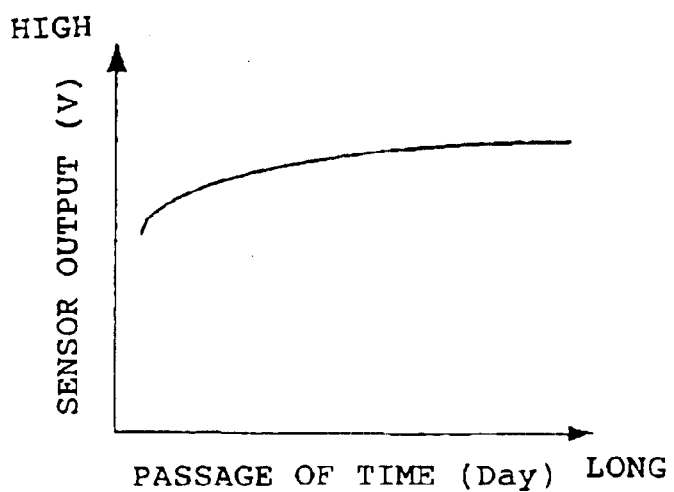

However, as in the case of the ultrasonic sensor of the first embodiment, the sensor output contains errors stemming from variation in the content of H2O (moisture) and stemming from zero-point drift of the sensor over time. That is, as shown in FIG. 12(a), when H2O adheres to the surface of the sensor, the sensor output increases, with the result that the gas concentration is measured to be lower than the actual level. Further, as shown in FIG. 12(b), when the output stability deteriorates over time, and thus the zero-point drifts, the sensor output increases, with the result that the gas concentration is measured to be lower than the actual level.

Therefore, in the present embodiment as well, the influence of moisture and zero-point drift over time can be eliminated when zero-point correction is performed in the same manner as in the first embodiment, so that the concentration of purge gas can be measured accurately. Accordingly, the concentration of purge gas can be properly controlled.

In the present embodiment, there is described an oxide semiconductor sensor utilizing tin oxide. However the above-described zero-point correction can also be applied to a contact-combustion-type sensor and like sensors.

In the contact-combustion-type sensor, a base material such as platinum is coated with a large number of catalyst elements, and variation in electrical resistance upon absorption and release of gas to and from the surface of the sensor is detected. Since sensors of this type have the same problem, the above-described zero-point correction enables precise measurement of gas concentration.

3. Third Embodiment:

Next, a third embodiment of the present invention will be described.

The present embodiment differs from the first and second embodiments in that a different type of a gas concentration sensor is used. Descriptions for the same portions as those of the first and second embodiments are omitted or simplified.

The present embodiment employs a gas concentration sensor which uses an element formed of solid electrolyte such as zirconia ceramic, and in which variation in electromotive force is utilized.

In the gas concentration sensor of the above-described type, through gas reaction, a difference in gas concentration is produced between a reaction electrode and a reference electrode, which form a concentration cell, and the thus-produced difference is detected as the electromotive force of the concentration cell. Sensors of this type also have a problem of generating errors due to instability (variation over time) of the sensor output and influence of moisture and the like. Therefore, the above-described zero-point correction enables precise measurement of gas concentration.

4. Fourth Embodiment:

Next, a fourth embodiment of the present invention will be described.

The present embodiment differs from the first through third embodiments in that a different type of a gas concentration sensor is used. Descriptions for the same portions as those of the first through third embodiments are omitted or simplified.

The present embodiment employs a gas concentration sensor of an FET type in which the gate voltage changes with gas concentration.

In the gas concentration sensor, an organic film which reacts with the above-described gas is formed on the gate electrode. When the gas concentration changes, the gate voltage changes due to a difference in amount of ions, so that the source-drain current changes with the gate voltage. The change in the source-drain current is detected for measurement of gas concentration. Sensors of this type also are liable to be affected by moisture. Therefore, the above-described zero-point correction enables precise measurement of gas concentration.

5. Fifth Embodiment:

Next, a fifth embodiment of the present invention will be described.

The present embodiment differs from the first through fourth embodiments in that a different type of a gas concentration sensor is used. Descriptions for the same portions as those of the first through fourth embodiments are omitted or simplified.

The present embodiment employs a gas concentration sensor of a calorie metric type in which a heater is used.

In the gas concentration sensor, gas is oxidized by means of a catalyst layer formed on a platinum heater, and differences in amount of heat generated through the oxidation reaction are measured through detection of variation in the electrical resistance of the heater. Sensors of this type also have a problem of being affected by moisture and variation over time. Therefore, the above-described zero-point correction enables precise measurement of gas concentration.

6. Sixth Embodiment:

Next, a sixth embodiment of the present invention will be described.

The present embodiment differs from the first through fifth embodiments in that a different type of a gas concentration sensor is used. Descriptions for the same portions as those of the first through fifth embodiments are omitted or simplified.

The present embodiment employs a gas concentration sensor of a type in which the electrostatic capacity between the electrodes changes when vaporized fuel enters the sensor.

In the gas concentration sensor, two electrodes are disposed within a gas passage. Taking advantage of the fact that the dielectric constant changes with gas concentration, change in gas concentration is detected in the form of variation in the electrostatic capacity between the electrodes. Sensors of this type also have a problem of generating errors due to influence of moisture and substances which deposit on the surface of the electrodes during long-term use. Therefore, the above-described zero-point correction enables precise measurement of gas concentration.

The present invention is not limited to the above-described embodiments, and may be practiced in various manners without departing from the scope thereof.

(1) Although in the above-described embodiments correction is performed during cranking after key-on, the zero-point correction of the gas concentration sensor may be performed at a timing other than the cranking period, at which the concentration of purge gas can be measured in a state in which supply of purge gas is stopped.

(2) In the above-described embodiment, concentration of purge gas is measured by use of a gas concentration sensor. However, the present invention can be applied to other cases such as a case in which the concentration of vaporized fuel supplied from a vaporized fuel generator is measured.

As described above, in the method of using a gas concentration sensor and the controller for a gas concentration sensor according to the present invention, a reference gas (e.g., only intake air) is measured by use of a gas concentration sensor before supply of a specific purge gas such as purge gas. Therefore, the degree of deterioration of the gas concentration sensor and the degree of influence of miscellaneous gases and the like can be detected.

Accordingly, when zero-point correction is performed in accordance with the degree of deterioration and influence of miscellaneous gases and the like, gas concentration can be determined accurately, with influence of moisture, deposits, and the like being eliminated.

Accordingly, the amount of a specific purge gas to be supplied can be adjusted precisely on the basis of the precise concentration of the specific purge gas, so that air-fuel ratio control and other various controls can be performed properly.

While the invention has been described in detail and with reference to specific embodiments thereof, it will be apparent to one skilled in the art that various changes and modifications can be made therein without departing from the spirit and scope thereof.

This application is based on Japanese Patent Application No. Hei. 11-4285 filed Jan. 11, 1999, and is incorporated herein by reference.

What is claimed is:

1. A method of using a gas concentration sensor which is disposed in an intake pipe of an internal combustion engine having an ignition key for cranking the engine so as to measure concentration of a specific purge gas contained in intake air, characterized in that on the basis of an output of the gas concentration sensor before supply of the specific purge gas to the intake pipe, variation in output of the gas concentration sensor is detected during cranking immediately after the ignition key is turned for the purpose of zero-point correction of the gas concentration sensor.

2. The method of using a gas concentration sensor according to claim 1, further characterized in that the zero-point correction is performed in accordance with the variation in the output of the gas concentration sensor.

3. The method of using a gas concentration sensor according to claim 1, further characterized in that an output value of the gas concentration sensor before the supply of the specific purge gas is compared with an output value which the gas concentration sensor must output when the specific purge gas is absent; and the zero-point correction is performed on the basis of the difference between the two output values.

4. The method of using a gas concentration sensor according to claim 1, further characterized in that when the concentration of the specific purge gas is measured in a state in which the specific purge gas is supplied, the concentration of the specific purge gas is determined in consideration of the correction amount of the zero-point correction.

5. The method of using a gas concentration sensor according to claim 1, characterized in that the specific purge gas is a combustible gas.

6. The method of using a gas concentration sensor according to claim 1, further characterized in that variation in the output of the gas concentration sensor is detected before combustible gas is purged from a canister.

7. The method of using a gas concentration sensor according to claim 1, characterized in that variation in the output of the gas concentration sensor is detected before combustible gas is fed from a canister first through a purging operation performed after the ignition key is turned.

8. The method of using a gas concentration sensor according to claim 1, further characterized in that the gas concentration sensor measures the concentration of the specific purge gas on the basis of variation in the speed of sound.

9. The method of using a gas concentration sensor according to claim 1, further characterized in that the gas concentration sensor measures the concentration of the specific purge gas on the basis of variation in the electrical resistance of a sensor element.

10. The method of using a gas concentration sensor according to claim 1, further characterized in that the gas concentration sensor measures the concentration of the specific purge gas on the basis of variation in electromotive force of a sensor element.

11. The method of using a gas concentration sensor according to claim 1, further characterized in that the gas concentration sensor measures the concentration of the specific purge gas on the basis of variation in amount of heat generated in a sensor element.

12. The method of using a gas concentration sensor according to claim 1, further characterized in that the gas concentration sensor measures the concentration of the specific purge gas on the basis of variation in electrostatic capacity of a sensor element.

13. A controller for a gas concentration sensor which is disposed in an intake pipe of an internal combustion engine having an ignition key for cranking the engine so as to measure concentration of a specific purge gas contained in intake air, characterized in that on the basis of an output of the gas concentration sensor before supply of the specific purge gas to the intake pipe, variation in output of the gas concentration sensor is detected during cranking immediately after the ignition key is turned for the purpose of zero-point correction of the gas concentration sensor, comprising:

memory means for storing, as a reference output, an output of the gas concentration sensor when the concentration of the specific purge gas is 0%;

actual output detection means for detecting during cranking immediately after the ignition key is turned an actual output of the gas concentration sensor on the basis of an output of the gas concentration sensor before the specific purge gas is supplied into the intake pipe; and zero-point correction means for comparing the reference output and the actual output in order to correct the zero point of the gas concentration sensor.

14. The controller for a gas concentration sensor according to claim 13, further comprising:

measurement means for determining the concentration of the specific purge gas, on the basis of the output of the gas concentration sensor subjected to the zero-point correction.

15. The controller for a gas concentration sensor according to claim 13, further comprising:

adjustment means for adjusting supply of the specific purge gas on the basis of the output of the gas concentration sensor subjected to the zero-point correction.

* * * * *